United States Patent [19]
Dufresne

[11] Patent Number: 4,867,746
[45] Date of Patent: Sep. 19, 1989

[54] NEEDLE SHIELD

[75] Inventor: Christopher M. Dufresne, Hewitt, N.J.

[73] Assignee: Becton, Dickinson and Company, Franklin Lakes, N.J.

[21] Appl. No.: 197,367

[22] Filed: May 23, 1988

[51] Int. Cl.⁴ .............................................. A61M 5/32
[52] U.S. Cl. ..................................... 604/192; 604/263
[58] Field of Search ........................ 604/192, 263, 187

[56] References Cited

U.S. PATENT DOCUMENTS

| | | | |
|---|---|---|---|
| 2,854,976 | 10/1958 | Heydrich | 604/263 X |
| 3,658,061 | 4/1972 | Hall | 604/263 |
| 4,623,336 | 11/1986 | Pedicano et al. | 604/192 |
| 4,629,453 | 12/1986 | Cooper | 604/192 |
| 4,634,428 | 1/1987 | Cuu | 604/110 |
| 4,643,722 | 2/1987 | Smith, Jr. | 604/192 |
| 4,650,468 | 3/1987 | Jennings, Jr. | 604/110 |
| 4,654,034 | 3/1987 | Masters et al. | 604/192 |
| 4,659,330 | 4/1987 | Nelson et al. | 604/192 |

FOREIGN PATENT DOCUMENTS 0160849  4/1985  European Pat. Off. .

Primary Examiner—John D. Yasko
Attorney, Agent, or Firm—Robert P. Grindle

[57] ABSTRACT

An arrangement of needle shield is provided which may be attached to the hub of a syringe or multiple blood sample holder, which shield is flexible and moves out of the way of the needle point for insertion into the skin, and which moves automatically over the contaminated needle at the instant the needle is removed from the skin for shielding the user from accidental needle stick. The arrangement is in one piece and includes an elongated hood-like body which surrounds the needle, and includes at one end a blunt front end shield, and at the other end a mounting ring for frictionally engaging the hub of a needle holder or syringe. The body includes an integral lock which snaps over the needle for holding the shield body of the invention over the contaminated needle.

3 Claims, 2 Drawing Sheets

NEEDLE SHIELD

BACKGROUND AND STATEMENT OF THE INVENTION

Generally speaking, this invention relates to needle shields for protecting the user of a needle from needle stick. More particularly, this invention relates to needle shields of the kind used with medical applications so that the shield moves in place for protecting the user from needle stick and potential contamination from a used needle.

A great many new devices have been developed in recent years because of the advent of the AIDS virus and the spread thereof by contaminated needles. These developments include a simplified arrangement such as those taught, for example, in U.S. Pat. Nos. 4,623,336 and 4,654,034 in the form of a flared shield for insertion of a contaminated needle therein. The arrangements include the flared open end so that the user is protected during insertion of the contaminated needle into the shield. Other devices of this kind include U.S. Pat. No. 4,650,468 and the arrangement taught in European Patent Publication No, 0160849. All of these arrangements include some sort of flared or wide-mouth front end for insertion of the contaminated needle so that the user has a larger mark for insertion of contaminated needle in the shield.

An additional arrangement of device of the kind to which this invention is directed is taught in U.S. Pat. Nos. 4,629,453 and 4,634,428, both teaching involved arrangements for protective caps for used and contaminated needles. An additional arrangement for a closure system for storing hypodermic needles and for the transport and disposal thereof is taught in U.S. Pat. No. 4,643,722. That patent includes a side opening for dropping the entire contaminated needle into the container rather than inserting it through one end of the container.

Finally, U.S. Pat. No. 4,659,330 includes a mounting arrangement for mounting on a syringe body with the device including a hinge connection for swinging a needle shield into place over a contaminated needle once it has been used.

By contrast, with the invention here, a simplified arrangement of needle shield is provided with a press-fit mounting which may be secured to the needle hub of either a syringe barrel or a blood sample needle holder for taking blood samples. The arrangement herein may be frictionally positioned and press fitted onto such a hub. When so positioned, the arrangement herein moves into place automatically for shielding the needle prior to use, and at all other times except during the time when the needle is actually inserted into a patient.

The arrangement here includes a flexible elongated integral device which extends over and along the needle top and both sides thereof with a hood shield at one end for extending over the point of the needle. An additional important feature is that it may be utilized with one hand, leaving one hand free for other functions.

Thus, when the user wishes to insert the needle through a patient's skin, the blunt hood shield at the front end is pressed against the skin of a patient and the needle inserted into the patient for administering a medication, or for removing a blood sample for examination. Immediately after removal of the needle from the patient's skin, the shield of the invention moves automatically, with no manipulation required by the user, back into place over the point of the needle so that the user is immediately and automatically protected from any kind of accidental needle prick. The used needle, therefore, may be readily moved to a disposal container for removing the needle and the shield of the invention by dropping them into the container, while the point of the needle is maintained in a protected shielded manner.

As a further feature of the invention, the needle shield assembly of the invention includes a frictional locking arrangement which the user may utilize for pressing the shield of the invention over the needle for holding the shield firmly in place over the needle when it is not being used, before or after contamination.

Finally, the simple arrangement of needle shield taught herein may be comprised of an inexpensive single piece of flexible plastic produced on a mass production basis, making it inexpensive for single use applications.

Other objects and advantages of this invention will be apparent from the following description, the accompanying drawings and the appended claims.

IN THE DRAWINGS

DETAILED DESCRIPTION OF THE INVENTION

Figure 1:
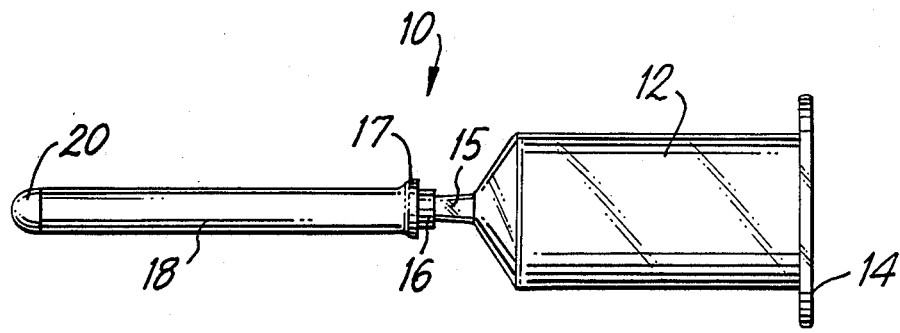
FIG. 1 is a top plan view of the assembly of the invention fixed to the hub of a conventional blood sample needle holder.

Referring to the drawings in which like reference characters refer to like parts throughout the several views thereof, FIG. 1 shows the needle shield assembly 10 of the invention fitted on the hub 16 of the neck 15 of a conventional blood sample needle holder 12. Needle holder 12 includes a finger grip arrangement 14 in the usual manner. One end 17 of the flexible needle shield body 18 is press fit onto hub 16, while the opposite end 20 thereof is in the form of a needle point hood 20.

Figure 3:
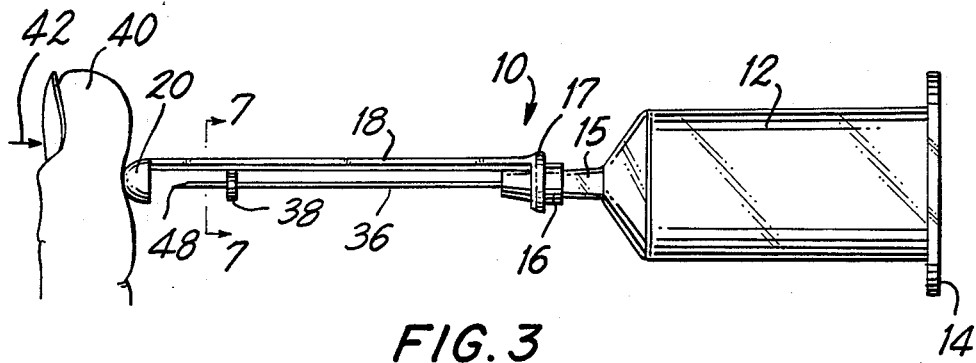
FIG. 3 is a longitudinal side elevational view of the embodiment of FIG. 1.

Referring to FIG. 3, the assembly of the embodiment of FIG. 1 is shown in a longitudinal side elevational view. As can be seen in FIG. 3, the longitudinal flexible body 18 forming the shield of the invention includes the flexible mounting grip or holder 17 which is press fit over hub 16 of holder 12. Mounting grip or holder 17 may be a partial ring which is snapped over hub 16, or a full ring which is slipped over hub 16 and, because of its flexible properties, pressed onto hub 16 in a frictional engagement. Hub 16 holds, in the usual manner, a needle 36 for insertion into a patient. As can be seen further in FIG. 3, the opposite end of shield 18 includes the blunt front end hood 20 which hangs over point 48 of needle 36. Thus, the finger 40 of the user is shielded from point 48, as shown in FIG. 3, if the user's finger 40 happens to move in the direction of arrow 42 in connection with the handling and use of the needle.

Further, while not necessary, assembly 10 may include a frictional locking guard 38 which depends from the flexible body 18 for gripping the needle and holding the flexible hood-like body 18 suspended over needle 36, once contamination of needle 36 has taken place.

Figures 4, 5:
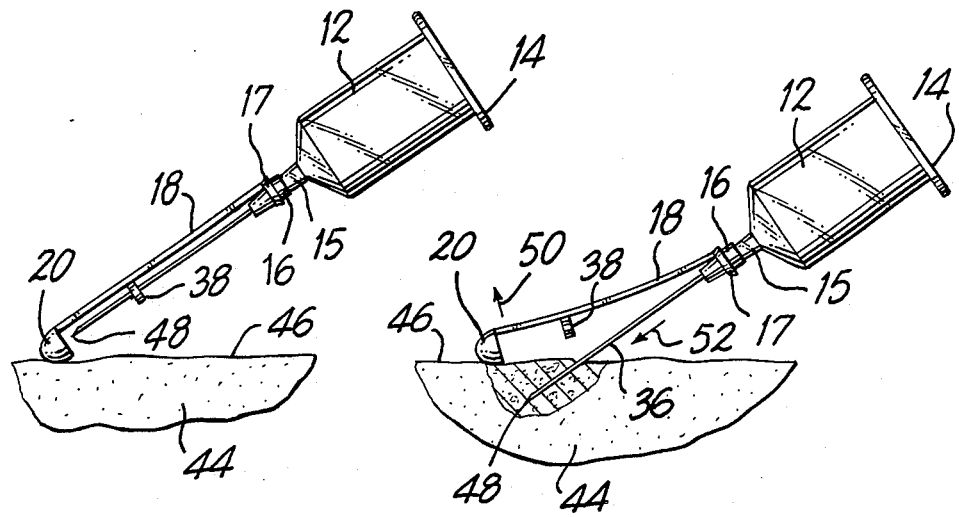
FIG. 4 is a view of the device in FIG. 3, reduced in size, and shown in the position immediately prior to the use thereof when a needle is being positioned for insertion into the skin of a patient.
FIG. 5 is a view of the assembly of FIG. 4 in a subsequent position wherein the needle is inserted into the skin of a patient.

Referring now to FIG. 4, the assembly 10 is shown in a position prior to the point 48 of needle 36 being inserted into the skin 44 of a patient. As can be seen in FIG. 4, the blunt front end hood 20 is resting against the patient's skin prior to any application of force by the technician for inserting needle 36 into the skin of a patient. Then, as shown in FIG. 5, the needle is moved in the direction of arrow 52 so that point 48 of needle 36 enters skin 44 of a patient. When this action takes place, the flexible elongated body 18 is flexed in the direction of arrow 50 so that the needle guard or holder 38 slips off of needle 36.

Once the needle 36 has been used and the point 48 thereof removed from the skin 44 of a patient, the flexible properties of the body 18 of the needle shield of the invention causes the shield to move back over the needle 36 for protecting the user from contamination. In doing so, the hooded curvature of the arrangement shown protects the user over the top of the elongated needle body as well as the point 48 thereof.

Figure 6:
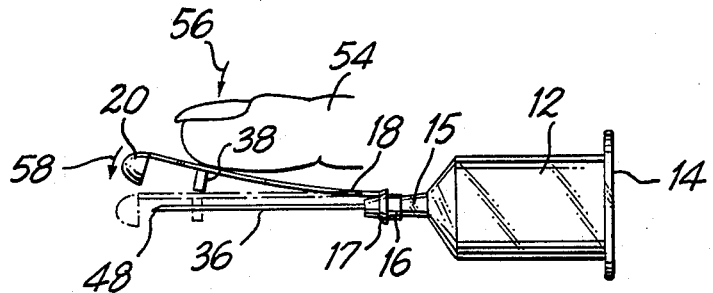
FIG. 6 is a longitudinal side elevational view of the assemblies of FIGS. 3, 4 and 5 shown after use of the needle wherein the flexible needle shield of the invention is being press fit by the user over the contaminated needle.

Of course, as shown in FIG. 6, the blunt front end of hood 20 moves in the direction of arrow 58 downwardly, as shown in FIG. 6 so as to protect the user from contaminated point 48. This allows single-handed maneuvering by the user. Then, if the assembly includes a snap-lock guard pressure by the finger 54 of the user moving in the direction of arrow 56 causes guard 38 to snap over the needle body 36 and hold the shield in place until such time as the entire assembly, including the shield and needle are removed from the hub 16 of holder 12, and dropped into a container for contaminated needles.

Figure 2:
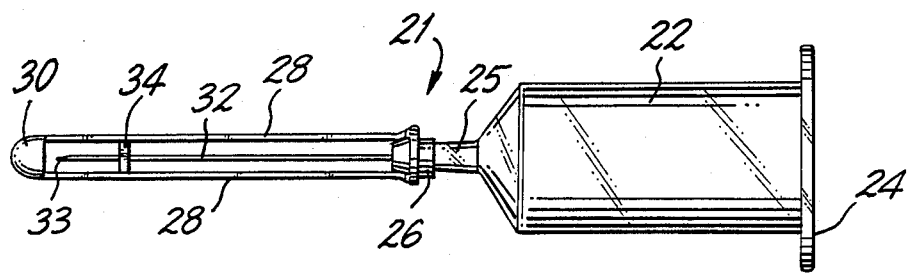
FIG. 2 is a top plan view of an additional embodiment of the assembly of the invention, also fixed to the hub of a conventional blood sample needle holder.

Referring now to FIG. 2, an additional embodiment of the invention is shown in the form of assembly 21. In this arrangement, the needle shield body is in the form of two elongated flexible side parts 28 extending along the side of a needle 32. These two side portions or halves 28 are a substitute for the flexible body 18 shown in the embodiment in FIG. 1. In this arrangement, the assembly 21 includes a front end hood 30 extending over the point 33 of needle 32, while the opposite end of the assembly includes a flared gripping ring arrangement for gripping hub 26 positioned on neck 25 of a holder 22, in the same manner as the embodiment shown in FIG. 1. The assembly 21 may also include a snap guard 34 in the same manner as guard 38 in the FIG. 1 arrangement for gripping needle 32. The arrangement 21 shown in FIG. 2 is arranged so that the user may observe the position of the needle 32 from the top prior to and during use, when it is inserted into the skin of a patient.

Figure 7:
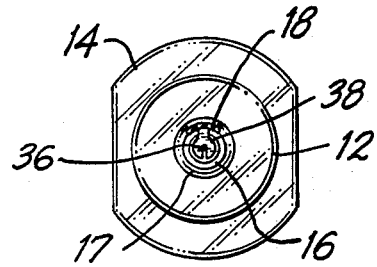
FIG. 7 is a sectional view taken along lines 7—7 of FIG. 3.

Finally, FIG. 7 shows a sectional view of the assembly in FIG. 3 taken along lines 7—7 of FIG. 3 and shows the arrangement of parts including the frictional gripping arrangement or guard 38 which depends from and is integral with elongated flexible shield body 18.

As can be seen, the snap lock arrangement 38 depends in a u-shaped form with a small opening at the bottom thereof for allowing passage of needle 36 therethrough.

Thus, as will be appreciated from the above, there is provided inaccordance with this invention a simple, inexpensive device for protecting the user of needles in medical applications from contamination brought on by accidental prick from such contaminated needles. The arrangement of the invention is so simple in its construction that it can be made in great quantities and thrown away after use with its associated needle.

The arrangement may be made by simple molding operations of a variety of thermoplastic materials which provide the flexibility necessary to impart the desired flexible property during use of the needle shield of the invention. Obviously, as will be understood by practitioners-in-the-art, this simplified arrangement herein may be comprised of a single piece of inexpensive plastic material which may be produced on a production line basis. Materials are selected which provide the degree of flexibility required for the purposes of the use of the invention herein.

While the forms of apparatus herein described constitute preferred embodiments of the invention, it is to be understood that the invention is not limited to these precise forms of apparatus and that changes may be made therein without departing from the scope of the invention which is defined in the appended claims. For example, the elongated body arrangement of the invention herein may be modified as long as it retains its flexible properties and allows for movement of the front end hood of the needle shield of the invention away from the needle during use while allowing for immediate automatic spring-back to the original position protecting the user from the point of the contaminated needle.

What is claimed is:

1. A needle shield for protecting a user from accidental needle stick, characterized by
    (a) an elongated flexible body for extending along a needle to be protected;
    (b) a flexible mounting grip integral with said flexible body;
    (c) said flexible mounting grip depending from one end of said flexible body for frictionally receiving a needle hub therein;
    (d) a flared needle point hood integral with said flexible body;
    (e) said hood depending from the end of said body opposite said flexible grip for shielding the point for shielding the point of a needle extending from a needle hub upon which said flexible ring is mounted;
    (f) said flexible body maintaining said hood constantly over the point of a needle extending from a needle hub upon which said flexible grip is mounted except when urged out of the way when the needle is used; and
    (g) said hood moving automatically over the needle point when not urged out of the way.

2. The needle shield of claim 1, further characterized by
    (a) said elongated flexible body having an elongated opening extending along the length thereof from said flexible mounting grip to said flared hood; and
    (b) said elongated opening allowing observation of a needle upon which said needle guard is mounted.

3. The needle shield of claim 1, further characterized by
(a) an integral needle locking guard depending from said elongated flexible body;
(b) said needle locking guard positioned at a point along said elongated flexible body spaced from said hood and said mounting grip; and
(c) said needle locking guard for holding said elongated flexible body against a needle upon which said needle shield is mounted for maintaining said hood over the point of a needle upon which said needle shield is mounted once the hood moves automatically over the needle.

* * * * *